(12) United States Patent
Dahnke

(10) Patent No.: US 6,369,049 B1
(45) Date of Patent: *Apr. 9, 2002

(54) TREATMENT OF MASTITIS

(75) Inventor: Karl Robert Dahnke, Carmel, IN (US)

(73) Assignee: Eli Lilly and Company, Indianapolis, IN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/289,934

(22) Filed: Apr. 12, 1999

Related U.S. Application Data

(60) Provisional application No. 60/083,662, filed on Apr. 30, 1998.

(51) Int. Cl.[7] .................... C07D 501/59; C07D 463/20; C07D 463/22; A61K 31/545; A61D 31/04
(52) U.S. Cl. ........................ 514/200; 514/208; 540/215; 540/229; 540/205; 540/301
(58) Field of Search ................. 540/215, 229; 514/208, 200

(56) References Cited

U.S. PATENT DOCUMENTS

| | | | |
|---|---|---|---|
| 3,907,784 A | 9/1975 | Huffman | 260/243 |
| 3,962,227 A | 6/1976 | Chauvette | 260/243 C |
| 4,261,991 A | 4/1981 | Webber | 424/246 |
| 4,379,149 A | 4/1983 | Hall | 204/72 |
| 4,521,598 A | * 6/1985 | Spry | 540/215 |
| 4,533,497 A | * 8/1985 | Spry | 540/215 |
| 4,708,956 A | 11/1987 | Tadashi et al. | 514/210 |
| 5,504,076 A | 4/1996 | Branch et al. | 514/206 |

FOREIGN PATENT DOCUMENTS

| | | |
|---|---|---|
| EP | 0 308 559 | 3/1989 |
| EP | 0 416 810 | 3/1991 |
| GB | 1 213 571 | 11/1970 |
| GB | 1 325 846 | 8/1973 |

OTHER PUBLICATIONS

Pfeil–Doyle, et al., *J. Med Chem.*, 31 (10), 1993–1997 (1988).
Snyder, et al., *Antimicrob Agents Chemother.*, 41 (8) 1649–1657 (1997).
Blaszczak, et al., *J. Med. Chem.*, 33 (6), 1656–1662 (1990).
Merck, et al., *Berlinger und Muenchener Tieraerztliche Wochenschrift*, 102 (8), 266–272 (1989).

* cited by examiner

*Primary Examiner*—Mark Berch
(74) *Attorney, Agent, or Firm*—John C. Demeter

(57) ABSTRACT

The invention provides new fluorinated cephalosporin antibiotics of Formula I

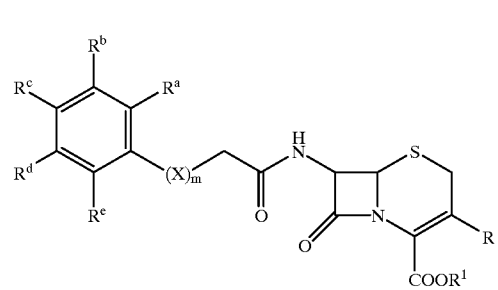

wherein $R^a$, $R^b$, $R^c$, $R^d$ and $R^e$, independently, are H, F or a $C_1$–$C_6$ alkyl-$(Z)_n$— group having at least one fluorine substituent;

X is O or S;

Y is S, O, or —$CH_2$—;

Z is O, S, —SO—, or —$SO_2$—;

m and n independently are 0 or 1; and $R^1$ is H, $C_1$–$C_6$-alkyl, phenyl or benzyl, each of which may optionally have up to three substituents selected from halo, $C_1$–$C_4$-alkoxy, phenyl, $NO_2$, $C_1$–$C_6$-alkanoyl, benzoyl, or $C_1$–$C_6$-alkanoyloxy; or a physiologically acceptable salt thereof;

and methods of preventing or treating or treating infection, particularly mastitis in ruminants, using these antibiotics.

21 Claims, No Drawings

TREATMENT OF MASTITIS

CROSS REFERENCE

This application claims the benefit of U.S. Provisional Application No. 60/083,662, filed Apr. 30, 1998.

BRIEF SUMMARY OF THE INVENTION

This invention relates to new fluorinated cephalosporin antibiotics and to formulations comprising, and methods of using, these antibiotics to control susceptible pathogens. The invention particularly relates to veterinary formulations and to methods for preventing or treating mastitis in a mammal with a fluorinated cephalosporin of this invention.

Mastitis is a serious problem, especially in the dairy industry. It is an inflammation of the udder caused by a number of different pathogens, including Staphylococcus species and Streptococcus species. There are, however, difficulties in treating mastitis effectively while still meeting the needs of the dairy industry. The agent used must be effective against the pathogen or pathogens causing the mastitis, must not adversely affect the animal being treated, and must be quickly cleared from the animal's system so that the milk it produces may be safe for subsequent use.

DETAILED DESCRIPTION OF THE INVENTION

This invention provides a new group of fluorinated cephalosporin compounds of formula I:

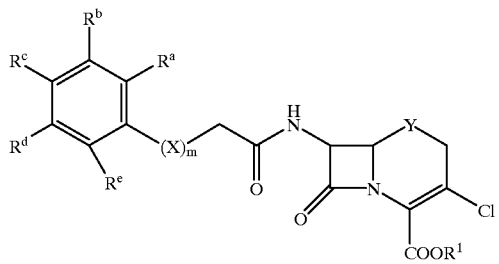

wherein $R^a$, $R^b$, $R^c$, $R^d$ and $R^e$, independently, are H, F or a $C_1$–$C_6$ alkyl-$(Z)_n$— group having at least one fluorine substituent;

X is O or S;

Y is S, O, or —$CH_2$—;

Z is O, S, —SO—, or —$SO_2$—;

m and n independently are 0 or 1; ; and $R^1$ is H, $C_1$–$C_6$-alkyl, phenyl or benzyl, each of which may optionally have up to three substituents selected from halo, $C_1$–$C_4$-alkoxy, phenyl, $NO_2$, $C_1$–$C_6$-alkanoyl, benzoyl, or $C_1$–$C_6$-alkanoyloxy;

or a physiologically acceptable salt thereof;

provided that:

1) at least one of $R^a$, $R^b$, $R^c$, $R^d$ or $R^e$ is other than hydrogen; and 2) when $R^c$ is F, or one of $R^b$ or $R^d$ is $CF^3$, at least one of the remaining $R^a$, $R^b$, $R^c$, $R^d$ or $R^e$ is other than hydgrogen.

The term "$C_1$–$C_n$-alkyl" refers to a straight or branched chain alkyl group having the designated number of carbon atoms. Examples include methyl, ethyl, isopropyl, n-pentyl, and the like.

The term "halo" refers to chloro, iodo, bromo or fluoro.

The formula I esters, i.e.. those compounds wherein $R^1$ is other than hydrogen or a salt form, act as pro-drugs. Thus, these compounds are converted in vivo to the corresponding free acid that has the desired activity. Certain Formula I esters are preferred. These esters include the pivaloyloxymethyl, acetoxymethyl, methoxymethyl, acetonyl, 1-(acetyloxy)ethyl and phenacyl.

Physiologically acceptable salts of the formula I compounds are also part of this invention. These salts include alkali-metal salts, e.g., sodium, potassium, etc., alkaline-earth metal salts, e.g., calcium, magnesium, etc., and salts with organic bases, such as organic amines, e.g., benzathine, pyridine, triethylamine, tripropylamine and triisopropylamine, etc. The triethylamine and sodium salts are particularly preferred salts.

The formula I compounds are active both in vitro and in vivo against various pathogenic organisms. In one aspect, they are active against certain pathogens that cause mastitis in mammals, particularly in ruminants. A special benefit of the formula I compounds is that they are active at levels such that they may provide improved control of mastitis over products currently used in the dairy industry.

This invention provides, therefore, a method of preventing or treating mastitis in a mammal that comprises administering to the mammal an amount of a formula I compound that effectively prevents or treats the mastitis. This method is particularly useful for preventing or treating mastitis in a ruminant.

The formula I compounds are especially useful for preventing or treating mastitis in cattle, goats and sheep. In one embodiment of this invention, the formula I compound is administered as the animal is lactating ("wet cow" therapy). In this embodiment the milk will be discarded until the mastitis has been successfully treated and the drug has cleared the animal, i.e., the drug is no longer present in the milk. The compounds of this invention may also be used for "dry cow" therapy, that is when administration occurs after lactation, and the animal will thereafter be managed as a dry cow with no further milking until the next parturition. In still another aspect, the formula I compound can be used prophylactically by administering it to a non-lactating animal, such as a nulliparous heifer, in the period prior to parturition.

The formula I compounds can be administered by a variety of methods, such as intramuscularly, subcutaneously, intravenously, intranasally, orally or by intramammary infusion. When used for preventing or treating mastitis, they are preferably administered by intramammary infusion.

It is understood in the art that the amount of formula I compound administered should be the amount that is effective to control the particular pathogen or pathogens in question. In addition, the type, size and condition of the host being treated must be taken into consideration. For example, when controlling a pathogen responsible for mastitis, the dose will vary depending on the type and size of the ruminant being treated.

As an illustration, when treating mastitis in cows amounts of from about 10 to about 1000 milligrams per quarter are generally effective to control the mastitis. Doses of about 50 to 300 mg per quarter are preferable; and doses of about 100 to 200 mg per quarter are most effective. In goats, on the other hand, amounts of from about 10 to about 100 milligrams per half are generally sufficient; doses of about 10 to 30 mg per half are preferred; and a dose of 20 mg per half is most preferred. An effective amount may be achieved by multiple dosings.

This invention also provides a veterinary or pharmaceutical formulation comprising a Formula I compound and one or more physiologically acceptable carriers. The veterinary formulations of this invention are particularly useful for preventing or treating mastitis in a mammal, especially a ruminant. Preferred ruminants are cattle and goats.

The formula I compounds can be formulated for veterinary or pharmaceutical administration according to methods understood in the art. When the compound is to be used in a veterinary formulation for preventing or treating mastitis, the formulation is preferably one that can be administered by intramammary infusion. For this type of infusion, the compound may be formulated in an oily base, e.g., a vegetable oil such as peanut oil or a non-vegetable oil such as mineral oil. The formulation may include a thickening agent and optionally also a surfactant.

When a formula I compound is to be administered to a mammal, for the treatment of other types of infections, it may be preferable to administer it in a pharmaceutical formulation comprising one or more pharmaceutically acceptable excipients. The preparation of such formulations is also understood in the art. See, for example, *Remington the Science and Practice of Pharmacy*, (Mack Publishing Co., Easton, Pa., 1995).

In preparing a veterinary formulation other than for intramammary infusion, or a pharmaceutical formulation, the formula I compound is usually mixed with an excipient, diluted by an excipient or enclosed within a carrier that can be in the form of a capsule, sachet, or other container. When the excipient serves as a diluent, it can be a solid, semi-solid, or liquid material that acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions and sterile packaged powders.

During the preparation of the formulation, it may be necessary to mill the active compound to provide the appropriate particle size prior to combining it with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh. When the compound is to be used in a formulation for intramammary infusion, it is preferable that the particle size be less than 100 microns and even more preferable that it be about 10 microns.

Examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so they provide quick, sustained or delayed release of the active ingredient after administration to the host by procedures known in the art.

For oral administration, the compound can be admixed with carriers and diluents and molded into tablets or enclosed in gelatin capsules.

The formula I compounds can be prepared by methods well understood in the art of cephalosporin antibiotics. Thus, for example, a 3-chloro-7-aminocephalosporanic acid is coupled with the acid halide of the corresponding side chain to be attached at the 7 position.

The following examples illustrate the compounds, methods and formulations of this invention.

EXAMPLE 1

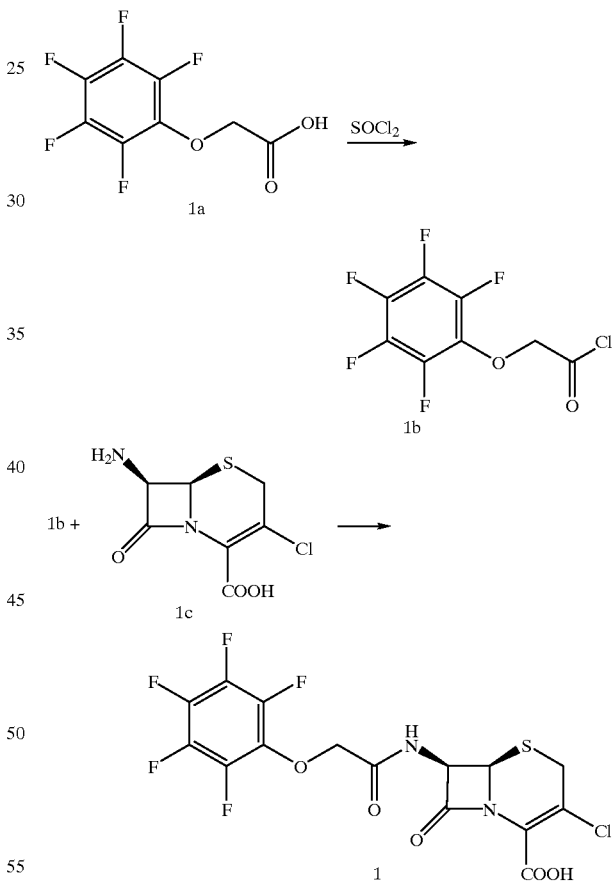

Step 1: Preparation of 1b

Thionyl chloride [8.85 g (5.4 mL), 74.3 mmol] was added to acid 1a (15.2 g, 62.0 mmol) in a 25-mL round-bottom flask. The mixture was heated to reflux (where it became a colorless solution) and maintained there for 1 hr. The solution was cooled, and the excess thionyl chloride was removed on a rotary evaporator at 25 mBar. The remaining solution was distilled at 0.25–0.3 mBar at 56–60° C. to give 14.9 g of 1b as a colorless liquid (92% yield).

Step 2: Preparation of Compound 1

Cephalosporin nucleus 1c (4.46 g, 19.0 mmol) was dissolved by suspending it in $H_2O$ (200 mL) and adding satd. aqueous $K_3PO_4$ until the solution had a pH of 8. The resulting solution was cooled to 0° C., and acid chloride 1b (4.95 g, 19.0 mmol) was added in portions over a 30-min period. $K_3PO_4$ was also added to keep the pH at about 8. The solution was allowed to warm slowly until solids began to precipitate. EtOAc (150 mL) was added, and the solution that resulted was acidified to pH 1 with 1N HCl. The aqueous layer was reextracted with EtOAc (2×150 mL).

The organic extracts were stirred for 1 hour with activated carbon; the carbon was removed by filtration; and the solution was then evaporated under vacuum to give 8.33 g of an off-white solid. The solid was suspended in diethyl ether and filtered to give 4.66 g of 1, m.p. 164° C. (dec); ms=457.9;

Anal.: Calcd. C, 39.27; H, 1.76; N, 6.11 Found C, 39.35; H, 1.75; N, 5.87.

EXAMPLES 2–10

Using procedures analogous to those described in Example 1, other illustrative formula I compounds ($R^1$=H) were prepared. Tables 1 and 1a summarize these compounds and certain of their physical characteristics.

TABLE 1

Illustrative Formula I Compounds[a]

| Compound | $R^a$ | $R^b$ | $R^c$ | $R^d$ | $R^e$ | X | Y | m |
|---|---|---|---|---|---|---|---|---|
| 1 | F | F | F | F | F | O | S | 1 |
| 2 | H | H | $CF_3$ | H | H | S | S | 1 |
| 3 | H | H | $CF_3SO_2$ | H | H | S | S | 1 |
| 4 | F | F | F | F | F | — | S | 0 |
| 5 | F | H | F | H | F | O | S | 1 |
| 6 | H | F | H | F | H | O | S | 1 |
| 7 | F | F | F | F | F | O | C | 1 |
| 8 | H | H | $CF_3O$ | H | H | O | S | 1 |
| 9 | F | F | F | F | F | S | S | 1 |
| 10 | F | F | $CF_3$ | F | F | O | S | 1 |

[a]$R^1$ = H

TABLE 1a

Physical Characteristics of Formula I Compounds

| Compound | MW | MP | Mass Spec* |
|---|---|---|---|
| 2 | 452.862 | 158° C. (dec) | 452 |
| 3 | 516.927 | 195° C. (dec) | 516.9 |
| 4 | 442.751 | 202° C. (dec) | 443 |
| 5 | 422.766 | 176° C. (dec) | 423.1 |
| 6 | 404.776 | 183° C. (dec) | 404.1 |
| 7 | 440.707 | 135° C. (dec) | 441.1 |
| 8 | 452.792 | 97° C. (dec) | 453.0 |
| 9 | 474.813 | 182° C. (dec) | 473.8 |
| 10 | 508.753 | 76–79° C. | 509.1 |

*FD-MS (m + 1)

EXAMPLE 5

Tables 2 and 2a summarize the minimal inhibitory concentrations (MIC's) at which illustrative formula I compounds and cephalothin inhibit certain microorganisms that are associated with mastitis, such as *Staphylococcus aureus* 10092 (Newbould strain).

TABLE 2

Comparison of In vitro Activity of Formula I Compounds and Cephalothin vs. *Staphylococcus aureus* and Streptococcus sp

| | MIC[a] vs. | | | | | | | |
|---|---|---|---|---|---|---|---|---|
| Compound No. | S. aureus ATCC 29213 | S. aureus 174 C | S. aureus 10092 | S. aureus F1C | Streptococcus uberis 150 L | Streptococcus uberis 166 L | Streptococcus agalactiae 150 B | Streptococcus dysgalactiae |
| 1 | 0.5 | 0.5 | 0.25 | 0.5 | 0.25 | 0.25 | 0.125 | 0.125 |
| 2 | 0.5 | 0.25 | 0.25 | 0.5 | O.25 | 0.25 | 0.5 | 0.25 |
| 2 | 0.25 | 0.125 | 0.125 | 0.25 | <0.0078 | <0.0078 | 0.0625 | <0.0078 |
| 4 | 1 | 1 | 0.5 | 1 | 0.5 | 0.0156 | 0.5 | 0.0312 |
| Cephalothin | 0.25 | 0.25 | 0.125–0.25 | 0.25 | 0.125 | 0.0625 | 0.125 | 0.0625–0.125 |

[a]Incubated at 37° C. overnight

TABLE 2a

Comparison of In vitro Activity of Formula I Compounds and Cephalothin vs. Staphylococcus sp and Streptococcus sp

| Organism | | Compound | | | | | |
|---|---|---|---|---|---|---|---|
| | Strain | 9 | 5 | 6 | 7 | 8 | Cephalothin |
| *Staphylococcus aureus* | 10,092 | 0.5 | 1 | 0.5 | 4 | 1 | 0.5 |

TABLE 2a-continued

Comparison of In vitro Activity of Formula I Compounds and
Cephalothin vs. Staphylococcus sp and Streptococcus sp

| Organism | Strain | Compound | | | | | Cephalothin |
|---|---|---|---|---|---|---|---|
| | | 9 | 5 | 6 | 7 | 8 | |
| Staphylococcus epidermidis | 174B | 0.5 | 1 | 0.5 | 2 | 1 | 0.5 |
| Staphylococcus aureus | 168H | 0.5 | 2 | 2 | 16 | 1 | 0.5 |
| Streptococcus agalactiae | 150G | 0.5 | 1 | 0.5 | 2 | 1 | 0.5 |
| Streptococcus uberis | 167I | 4 | 16 | 32 | 128 | 128 | 32 |
| Streptococcus dysgalactiae | 152B | 0.5 | 0.5 | 0.25 | 2 | 0.5 | 0.5 |
| Staphylococcus aureus | 170C | 0.5 | 4 | 4 | 1 | <0.125 | 0.5 |
| Streptococcus faecalis | — | 8 | 16 | 32 | >128 | 64 | 16 |

The formula I compounds are also active against certain Gram-negative species. Tables 3 and 3a show the MIC's of Formula I compounds against certain Gram-negative species.

TABLE 3

Comparison of in vitro Activity of Compound 1 and
Cephalothin against Gram-Negative Organisms

| | MIC[a] | |
|---|---|---|
| Organism | Compound 1 | Cephalothin |
| Pasteurella multocida 108E (bovine) | 0.5 | 0.5 |
| Pasteurella multocida ATCC 12945 | 0.125 | 0.25 |
| Pasteurella multocida 1051 (swine) | 0.5 | 0.25 |
| Pasteurella multocida 10,102 (bovine) | 0.5 | 0.5 |
| Pasteurella haemolytica 114F (bovine) | 4 | 1 |
| Pasteurella haemolytica 128K (bovine) | 4 | 0.5 |
| Pasteurella haemolytica 129R (bovine) | 4 | 1 |
| Salmonella typhimurium | >128 | 4 |
| Escherichia coli | >128 | 8 |

[a]Incubated at 37° C. overnight

TABLE 3a

Comparison of in vitro activity of Formula I Compounds
against Pasteurella haemolytica[a]

| Compound | MIC[b] |
|---|---|
| 5 | 16 |
| 6 | 4 |
| 7 | 32 |
| 8 | 32 |
| 9 | 4 |
| Cephalothin | 1 |

[a]Strain 128K
[b]Incubated at 37° overnight

EXAMPLE 13

Efficacy of Formula I Compounds in an Induced
*Staphylococcus Aureus* Mastitis Model in Lactating
Goats Sixteen lactating goats were selected based on the absence of *Staphylococcus aureus* in pre-challenge milk cultures. Maintenance ration was provided to the animals throughout the study. The goats were milked twice each day using a portable goat milker.

Milk samples were collected during the morning milking. One day prior to challenge, milk culture samples were collected from each half of the test animals to determine if there was a pre-existing infection. Additionally, a sample was collected from each half for Somatic Cell Count (SCC) determination. A milk culture sample and a sample for SCC were collected from each half 24 hours post-challenge and on Days +4 to +6, +8, +11, +13, and +15.

Udder scoring was performed during each milking using the following table:

| Severity Score | Description |
|---|---|
| 1 | Normal milk - no udder swelling |
| 2 | Normal milk - udder swelling |
| 3 | Abnormal milk - little or no udder swelling |
| 4 | Abnormal milk and udder swollen, tender, or hot. Acute clinical mastitis. |
| 5 | Acute clinical mastitis with systemic involvement. |

General health observations and body temperature were recorded once a day following milking during the challenge and treatment periods.

Milk samples were submitted for analysis for SCC using an electronic somatic cell counting system.

Milk culture samples were assayed for bacterial culture by plating 1.0 mL and 0.1 mL of the milk sample directly onto duplicate blood agar plates. Additionally, dilutions 10⁻ of the milk sample were plated. Plates were incubated overnight at 37° C.

*Staphylococcus aureus* 10092 (Newbould) was used as the challenge strain. The challenge culture was grown in Tryptic Soy Broth (TSB) from a lyovial stock overnight (16 hours) at 37° C. TSB (100 mL) was inoculated with 1 mL of the overnight culture and incubated at 37° C. with shaking for 4 hours. The culture was centrifuged at 9000 rpm for 10 minutes at 10° C.; supernatant was removed and the pellet was resuspended in phosphate buffered saline (PBS). Optimum O.D. reading at 650 nm was approximately 0.035. A 10-fold dilution series was prepared with saline to determine the CFU/mL, plating $10^{-5}$, $10^{-6}$, and $10^{-7}$ dilutions onto duplicate blood agar plates. The $10^{-7}$ dilution (approximately 10 CFU/mL) was used for the challenge material, yielding a challenge of 50 CFU/half with a 5-mL infusion.

Sixteen goats were used for the trial. During a one day pre-challenge period, milk samples were collected and temperatures were taken during the morning milking. Milk/udder evaluations were documented during the morning and afternoon milkings.

Staphylococcus aureus 10092 was infused into both halves in each of the goats. The goats were challenged following the morning milking and milked in the afternoon on the day of challenge. The challenge inoculum volume was 5 mL/half containing approximately 50 CFU S. aureus.

For the 24 hr post-challenge period milk samples were collected during the morning milking, and milk/udder evaluations made during the morning and afternoon milking.

Treatment was started at 36 hours post-challenge. Milk samples were collected for culture and SCC 24 hours post-challenge, prior to the morning milking, and the treatment period started following the afternoon milking.

Eight halves (4 goats) each were treated for 2 consecutive milkings 12 hours apart, following milking. Each designated compound was formulated in peanut oil with 45 μmoles of compound per 5 g of formulation to give approximately 25 mg/5 mL dose.

Following treatment, the goats were milked and observed for 15 days. Milk samples were collected on Days +4 to +6, +8, +11, +13, and +15 to determine if the infection had cleared.

Establishment of mastitis was determined by bacterial culturing, severity of udder scoring, somatic cell count results, and body temperature.

On Days +2 to +6, milk samples were collected for a colorimetric assay to determine whether the antibiotic was still present in the milk.

Table 4 summarizes the activity of typical formula I compounds in this assay.

TABLE 4

In vivo Efficacy of Formula I Compounds vs.
Staphylococcus aureus-Induced Mastitis in Goats

| Compound | % Bacteriologic Cures |
|---|---|
| 1 | 75* |
| 2 | 50 |
| 5 | 100 |
| 6 | 75 |
| 7 | 13 |
| 8 | 50 |
| 9 | 63 |
| 10 | 57 |

*Dosing was 100 mg/5 mL dose

I claim:
1. A compound of the formula

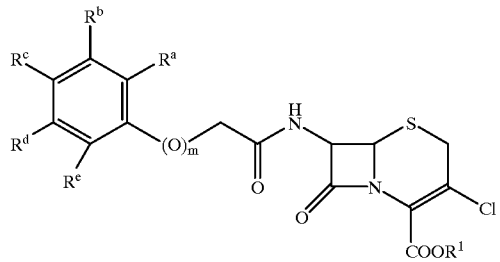

wherein
$R^a$, $R^b$, $R^c$, $R^d$ and $R^e$, independently, are H, F or a $C_1$–$C_6$ alkyl-$(Z)_n$— group having at least one fluorine substituent;
Z is O, S, —SO—, or —SO$_2$—;
m and n independently are 0 or 1; and
$R^1$ is H, $C_1$–$C_6$-alkyl, phenyl or benzyl, each of which may optionally have up to three substituents selected from halo, $C_1$–$C_4$-alkoxy, phenyl, NO$_2$, $C_1$–$C_6$-alkanoyl, benzoyl, or $C_1$–$C_6$-alkanoyloxy;
or a physiologically acceptable salt thereof;
provided that:
1) at least one of $R^a$, $R^b$, $R^c$, $R^d$ or $R^e$ is other than hydrogen; and
2) when $R^c$ is F, or one of $R^b$ or $R^d$ is CF$_3$, at least one of the remaining $R^a$, $R^b$, $R^c$, $R^d$ or $R^e$ is other than hydrogen.

2. A compound of the formula:

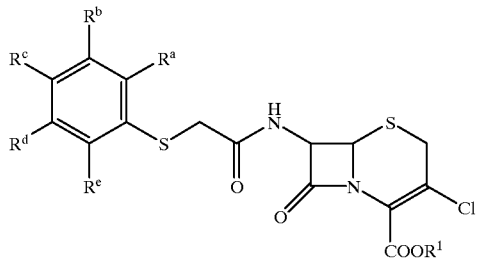

wherein
$R^a$, $R^b$, $R^d$ and $R^e$, independently, are H, F or a $C_1$–$C_6$ alkyl-$(Z)_n$— group having at least one fluorine fluorine substituent;
$R^c$ is a $C_1$–$C_6$ alkyl-$(Z)_n$—group having at least one substituent;
Z is O, S, —SO—, or —SO$_2$—;
n is O or 1; and
$R^1$ is H, $C_1$–$C_6$-alkyl, phenyl or benzyl, each of which may optionally have up to three substituents selected from halo, $C_1$–$C_4$-alkoxy, phenyl, NO$_2$, $C_1$–$C_6$-alkanoyl, benzoyl, or $C_1$–$C_6$-alkanoyloxy;
or a physiologically acceptable salt thereof.

3. A method of preventing or treating mastitis in a mammal that comprises administering to the mammal an effective amount of a compound of claim 2.

4. A method of claim 3 wherein the mammal is a ruminant.

5. A compound of claim 1 wherein m is 1.

6. A veterinary formulation comprising a compound of claim 2 and a physiologically acceptable carrier.

7. A compound of claim 1 wherein m is 0.

8. A compound of claim 5 wherein $R^1$ is H or its sodium salt.

9. A compound of claim 5 wherein $R^1$ is F.

10. A compound of claim 5 wherein $R^c$ is $CF_3O$.

11. A compound of claim 2 wherein $R^c$ is $CF_3SO_2$.

12. A compound of claim 2 wherein $R^c$ is —$CF_3$.

13. A compound of claim 7 wherein $R^c$ is F.

14. A veterinary formulation comprising a coupound of claim 1 and a physiologically acceptable carrier.

15. A method of preventing or treating mastitis in a mammal that comprises administering to the mammal an effective amount of a compound of claim 1.

16. A method of claim 15 wherein the mammal is a ruminant.

17. A method of preventing or treating mastitis in a mammal that comprises administering to the mammal effective amount of a compound of claim 11.

18. A method of preventing or treating mastitis in a mammal that comprises administering to the mammal effective amount of a compound of claim 12.

19. A method of preventing or treating mastitis in a mammal that comprises administering to the mammal an effective amount of a compound in claim 5.

20. A method of preventing or treating mastitis in a mammal that comprises administering to the mammal effective amount of a compound of claim 10.

21. A method of preventing or treating mastitis in a mammal that comprises administering to the mammal effective amount of a compound of claim 8.

* * * * *